United States Patent [19]

Lévêque et al.

[11] 4,159,640

[45] Jul. 3, 1979

[54] APPARATUS FOR MEASURING THE CONSISTENCY OR HARDNESS OF A MATERIAL

[75] Inventors: Jean-Luc Lévêque, Montfermeil; Gilbert Gras, Aulnay-Sous-Bois; Jean Scot, Paris, all of France

[73] Assignee: L'Oreal, Paris, France

[21] Appl. No.: 882,163

[22] Filed: Mar. 1, 1978

[30] Foreign Application Priority Data

Mar. 4, 1977 [FR] France .............................. 77 06505

[51] Int. Cl.$^2$ .............................................. G01N 3/42
[52] U.S. Cl. ......................................... 73/81; 128/774
[58] Field of Search .................... 73/81, 161; 128/2 R

[56] References Cited

U.S. PATENT DOCUMENTS

| 2,839,917 | 6/1958 | Webster | 73/81 |
| 3,309,916 | 3/1967 | Pearson | 73/81 |

Primary Examiner—Jerry W. Myracle
Attorney, Agent, or Firm—Brisebois & Kruger

[57] ABSTRACT

An apparatus for measuring the consistency or hardness of a material, for example skin tissue on a living body, comprises a support to be applied against the material to be tested and a feeler movably carried by the support for displacement through a distance which will be proportional to the hardness or consistency being measured. To avoid the need for careful positioning of the device on the test material with a carefully constant bearing pressure, a control circuit is provided for recording the displacement of the feeler only when the bearing pressure of the support on the test material has a predetermined value. The reading of the displacement is held and is preferably digital. Application of the support successively to different points on the test material will enable a true comparison of the readings at the various points.

14 Claims, 3 Drawing Figures

APPARATUS FOR MEASURING THE CONSISTENCY OR HARDNESS OF A MATERIAL

It is well known that in the context of research into the physical characteristics of a material, it is frequently desirable or necessary to study the hardness of this material. It has already been proposed to measure hardness by registering the displacement of a clearly defined feeler made to bear against the material to be studied with a predetermined force. For measuring hardness with an apparatus that is easily transportable, an apparatus is used for manual handling which is applied to the surface of the material to be tested. This kind of procedure permits satisfactory results to be obtained if the material to be tested is relatively rigid as is, for instance, the case with a metal or a rigid plastics material. On the other hand, when the material to be tested is relatively flexible and deformable, it has been found that the hardness measurements made with an apparatus with manual handling applied to the material do not yield reproducible results. This is the case, for instance, when such an apparatus is used to measure the rigidity or consistency of a living tissue, for instance, the consistency of a woman's breast.

The object of the invention is to propose an apparatus permitting the hardness or the consistency of a relatively non-rigid material to be measured in a reproducible way.

According to the present invention we provide apparatus for measuring the hardness of a material by application of the apparatus against the material to be tested, such apparatus comprising a support to rest on the material to be tested; a feeler carried by said support and arranged to bear on the said material with a predetermined force; and means for selectively and automatically detecting the displacement of the feeler only for a predetermined value $P_O$ of the bearing pressure of the apparatus on the material.

With the apparatus of this invention, adequately reproducible measurements have been obtained by measuring the displacement of the feeler resting on the material to be tested, since the precaution is taken of effecting the measurements with a rigorously constant bearing pressure of the apparatus on the material. Clearly it is difficult to maintain a rigorously constant bearing pressure of an apparatus with manual handling on a relatively flexible material. Thus with the apparatus of this invention provision is made for ensuring that although the apparatus may be applied to the material to be tested with a variable pressure, the displacement of the feeler is registered only at the time when the bearing pressure of the apparatus on the material is equal to the predetermined pressure at which it is desired to take the measurement. Thus one can manipulate the apparatus in accordance with the invention without having to take excessive care to maintain it steady, and can, nevertheless, obtain perfectly reproducible hardness measurements on a flexible material such as skin.

In a preferred embodiment, said means for selectively and automatically detecting the displacement of said feeler includes: a pressure detector arranged on said support at a zone where the support bears on the material, said pressure detector being responsive to the pressure of the apparatus on the said material; and means for comparing the output signal of the pressure sensor with a predetermined threshold and for actuating the display of the displacement of the feeler when this threshold is attained. The depth of displacement of the feeler of the apparatus into the test material is registered by a displacement sensor. The feeler is spring urged against the test material. The pressure sensor is an annular sensor arranged concentrically around the axis of said feeler. The displacement sensor delivers a signal, d.c. or a.c., whose voltage amplitude is substantially proportional to the displacement of the feeler. The pressure sensor delivers a signal, d.c. or a.c., whose voltage amplitude is substantially proportional to the bearing pressure of the apparatus on the material. The pressure sensor is energized with a low frequency alternating current and is constituted by a Wheatstone Bridge, two branches of which are elements which are pressure sensitive, for example membranes carrying semi-conductor deposits. The pressure sensor feeds a trigger device which registers the attainment, by the output voltage from the pressure sensor, of a predetermined value corresponding to pressure $P_O$, this trigger element actuating a monostable device whose rising signal front actuates recording of the voltage delivered by the displacement sensor. The voltage deriving from the displacement sensor is recorded at instants controlled by the trigger element. The voltage is recorded by a digital voltmeter. The monostable device actuates, after a predetermined time lag, the display of the voltage measured on the digital voltmeter, preferably via a bistable device.

It is clear that the apparatus in accordance with the invention facilitates manual use, but will nevertheless only register the displacement of the feeler at a given bearing pressure $P_O$ on the flexible material to be tested, where the same pressure value $P_O$ will apply for all separate readings taken.

The proportionate signal deriving from the displacement sensor is permanently measured by the digital voltmeter which gives a measurement at every metering interval defined by its built-in timer, although these successive different measurements will not be retained in display on the voltmeter; until the bearing pressure of the apparatus on the test material is equal to the predetermined $P_O$ value, the voltmeter "idles" and supplies illegible and constantly variable indications. When, during application of the apparatus progressively to the material to be tested, the pressure value $P_O$ is reached, the value of the signal supplied at this moment by the displacement sensor is recorded and the digital voltmeter which displays the value of the recorded displacement is locked. Preferably, the voltmeter is set with a slight time lag in relation to the recording action to avoid reading unwanted transient signals superimposed, during the interval of the control pulses on the voltage intended to be read.

In order that the present invention may more readily be understood, the following description is given, merely by way of example, of one embodiment represented on the accompanying drawings in which.

Figure 1:
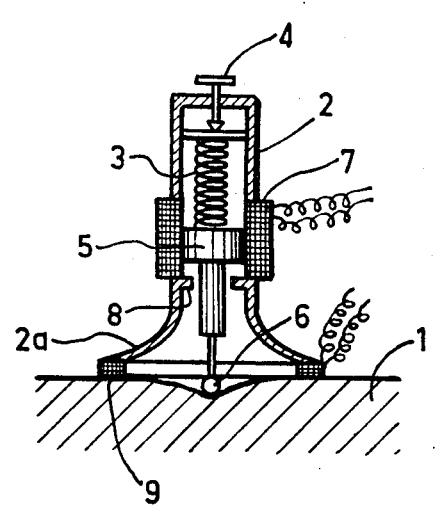
FIG. 1 is a schematic axial cross-section showing a measuring apparatus according to the invention.

Referring now to the drawings, there will be seen a material 1 to be tested; this may be a skin zone or the surface of a muscle or any other tissue, for example, the surface of a woman's breast whose consistency is required to be measured.

The measuring apparatus comprises a cylindrical housing 2 enclosing a spring 3 the degree of pre-straining of which, in compression, is adjustable by means of screw 4. The spring 3 pushes a sliding piston 5 towards the material 1, and the end of this piston fixedly carries a feeler 6. The displacement of piston 5 in the cylindrical housing 2 is registered by means of a conventional type of displacement sensor 7 which delivers a continuous voltage output proportional to the displacement of feeler 6 from a reference position. Housing 2 comprises stops 8 limiting the travel of piston 5 away from the screw 4, thereby defining the aforementioned reference position.

The part of housing 2 which is directly opposite the test material 1 is enlarged so as to constitute a kind of funnel 2a at the end of which there is an annular pressure sensor 9 constituting a circular ring concentric about the feeler 6. Pressure sensor 9 is conveniently a sensor of the type sold by the Entran Device Co. Inc. under reference ELF 1000; and is constituted by a Wheatstone Bridge, two branches of which are membranes coated by a semi-conductor coating. This sensor 9 is supplied with a 1 kHz alternating current by means of oscillator 10 and then has an alternating voltage output of the same frequency as the power supply but with the maximum voltage of the alternating output oscillations proportional to the bearing pressure of the housing 2 on material 1.

Figure 3:
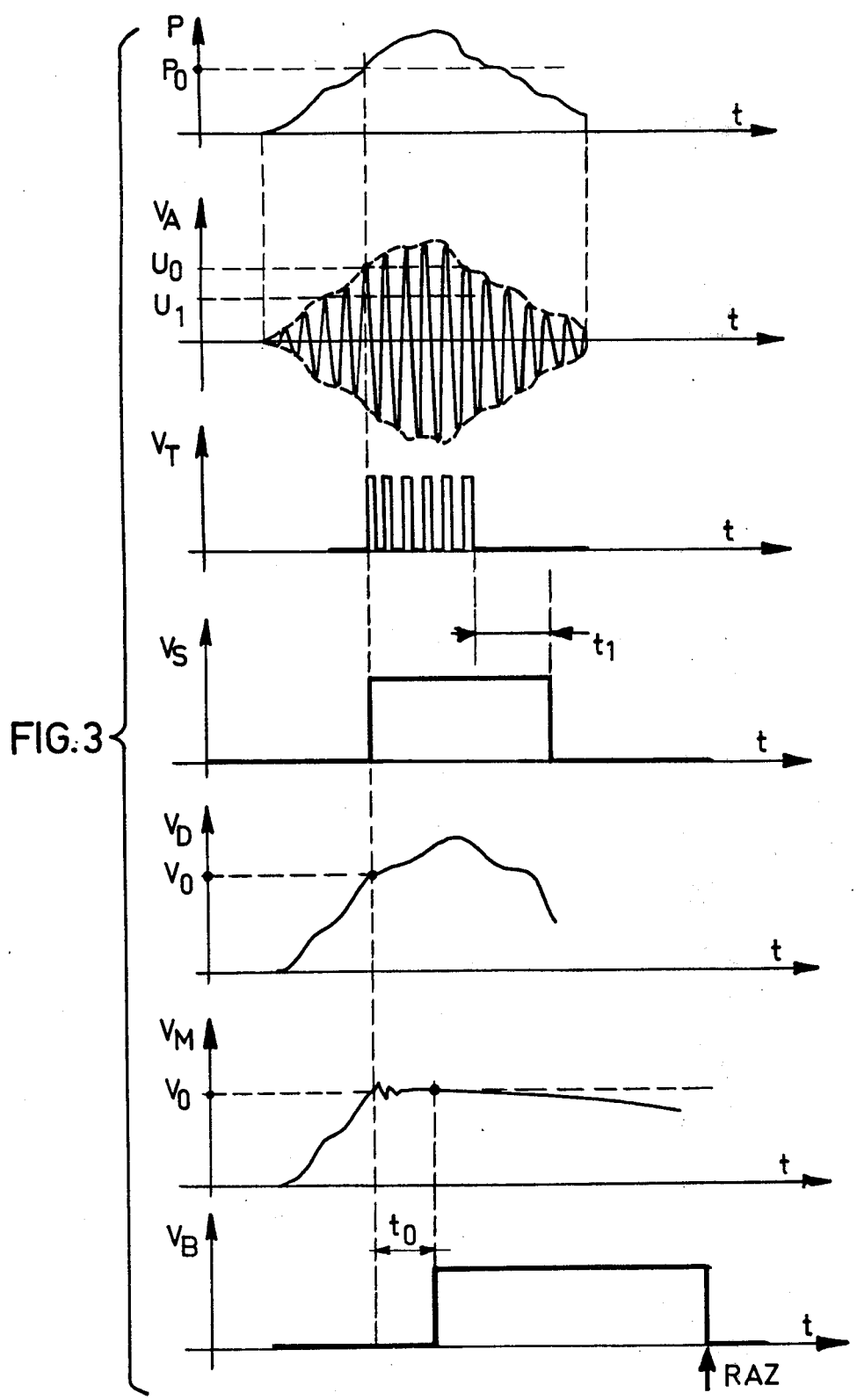
FIG. 3 shows the time curve of bearing pressure P of the apparatus on the test material and the voltages at various points of the circuit of FIG. 2.

On FIG. 3, the variations in bearing pressure P of the apparatus, with respect to time, when the user applies this apparatus to the material to be tested have been shown on the top line and the variations in the output voltage of sensor 9 (after amplification) have been shown on the second line.

Figure 2:
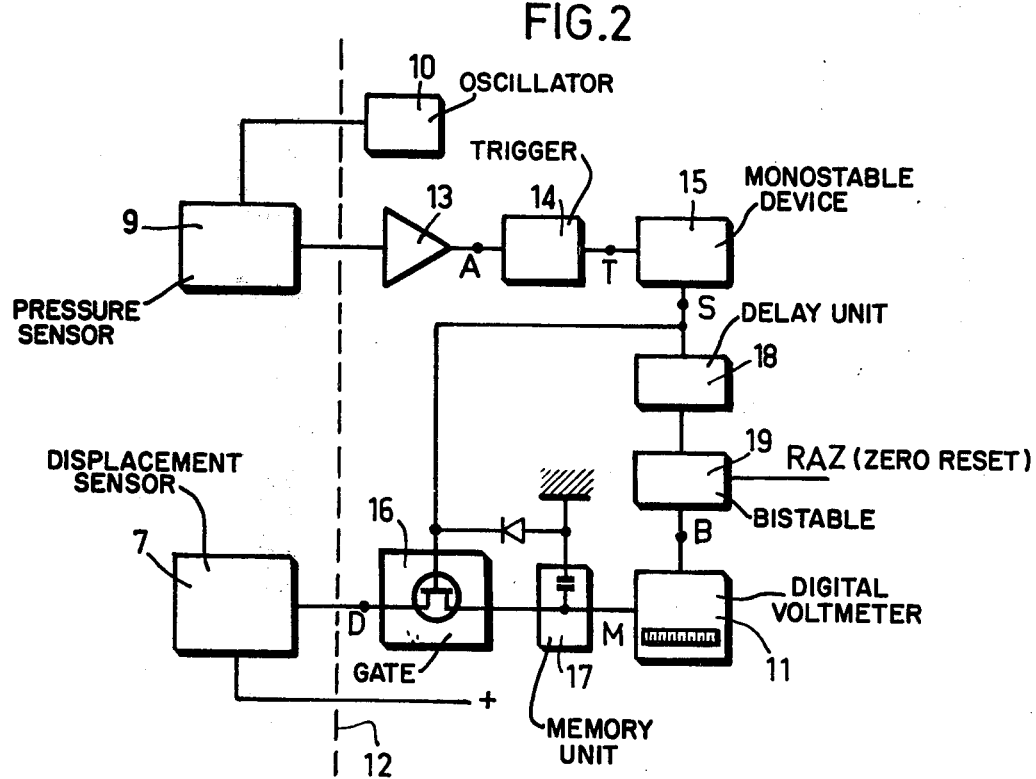
FIG. 2 is a block diagram of the electronic circuit linked to the apparatus of FIG. 1.

FIG. 2 shows the block diagram of an electronic circuit linked to the measurement apparatus of FIG. 1. The apparatus of FIG. 1 constitutes the movable unit of the measurement appartus and it is connected to a fixed control unit which includes the display device constituted, in this case, by a digital voltmeter 11. On FIG. 2, the broken line 12 separates the fixed unit of the apparatus (situated towards the right of the line 12) from the movable unit (situated to the left) shown in FIG. 1. The movable unit shown in FIG. 1 is connected to the fixed unit by electrical leads ensuring the power supply of the two sensors 7 and 9 and the transmission of the output signals from the two sensors 7 and 9.

The output signal of sensor 9 is sent to a frequency selective amplifier 13 turned to 1 kHz frequency. The output of amplifier 13 is a linear function of the bearing pressure of sensor 9 on the test material 1.

The second line of FIG. 3 shows the variation of voltage $V_A$ at point A at the output side of amplifier 13. This voltage $V_A$ is sent to a trigger device 14 which supplies an output signal $V_T$ with a constant amplitude and a frequency of 1 kHz when the input voltage $V_A$ attains the value of a high threshold $U_O$ of the trigger device 14, and this constant amplitude output signal is maintained while the input voltage $V_A$ remains above the value of a low threshold $U_1$ of trigger 14.

The third line of FIG. 3, shows the output signal $V_T$ of trigger 14. This voltage $V_T$ is sent to the input of a monostable device 15 whose output voltage $V_S$ is shown on the fourth line of FIG. 3. The voltage $V_S$ passes to its high level upon the rising front of $V_T$ and is held at that level both while signal $V_T$ remains established and during a time lag $T_l$ after the end of signal $V_T$.

The output voltage $V_S$ of the monostable device 15 is applied to a gate 16 constituted by a field effect transistor supplied by voltage $V_D$ from the displacement sensor 7.

The fifth line of FIG. 3, shows the variations in the voltage output of displacement sensor 7. When the monostable device 15 does not provide any signal, the transistor constituting gate 16 conducts and the supply voltage $V_D$ to this transistor can charge a capacitor constituting the memory unit 17.

The sixth line of FIG. 3, shows the voltage $V_M$ at the output of memory unit 17. As the rising front of signal $V_S$ (provided by the monostable device 15) occurs, the output voltage of displacement sensor 7 is $V_O$ and this voltage is again found at the ouput of memory unit 17. The rising front of signal $V_S$ blocks the transistor of gate 16 and the voltage $V_M$ will then remain constant save for a slight discharge of the capacitor constituting the memory unit 17. When the gate transistor is blocked, there will be some unwanted oscillations of voltage $V_M$ so it is preferable to record the value of voltage $V_M$ by reading the digital voltmeter 11 after a delay $t_O$ from the instant of blocking of the transistor of gate 16. The digital voltmeter 11 operates with a frequency given to it by a built-in timer, and the delay $t_O$ may be chosed to be equal to two counting periods of the voltmeter.

To hold the reading on the digital voltmeter at the moment following the blocking of the transistor of gate 16 (after the delay $t_O$) the signal $V_S$ emitted from monostable device 15 is used. This signal $V_S$ controls a retarding circuit 18 which in turn controls a bistable device 19 the output voltage $V_B$ of which is shown on last line of FIG. 3. The rising front of signal $V_B$ follows the rising front of signal $V_S$ (i.e. blocking of the transistor of gate 16) with delay $t_O$. While signal $V_B$ is at its high level, the digital voltmeter 11 is locked on the last reading taken. Voltmeter 11 is only unlocked when the bistable device 19 is manually reset to zero, this resetting to zero having been indicated by RAZ on FIGS. 2 and 3. Thus, the digital voltmeter 11 becomes locked to the reading of voltage $V_M$ at a time which follows the blocking of the transistor of gate 16 by a time delay $t_O$. Since time delay $t_O$ is small, the capacitor of circuit 17 has not had time to discharge to any significant extent and therefore the voltage $V_M$, as read, will have remained substantially equal to voltage $V_O$ which corresponded to the output of displacement sensor 7 when pressure $P_O$ was attained on pressure sensor 9.

It has been established that using the apparatus illustrated for the measurement of hardness or consistency of a relatively soft material as, for instance, a woman's breast, makes it possible to obtain perfectly reproducible values. Moreover, the dimensions of the movable unit of the apparatus (shown in FIG. 1) are rather small, thereby making it possible to study the variation in consistency between different zones of the same material by repositioning the apparatus manually on the material. The operation of this apparatus is extremely simple since once the digital voltmeter 11 has been released via the zero resetting control of bistable device 19, it is sufficient to apply the movable unit of FIG. 1 progressively to the material to be tested and to read the next displayed reading which will be locked on voltmeter 11 once the previous value of measurement pressure $P_O$ is again attained.

It should be noted that the design of the apparatus is extremely simple and leads to a reliable construction.

The embodiment described above is in no way restrictive and may be subject to any conceivable modifications without thereby departing from the scope of the invention claimed.

We claim:

1. Apparatus for measuring the hardness of a material by application of the apparatus against the material to be tested, comprising (a) a support (b) feeler means carried by said support for displacement relative to said support, (c) means for causing said feeler means to bear on the said material with a predetermined force; (d) a pressure sensor carried by said support for sensing the bearing pressure of the apparatus on said material and for providing an output signal indicative of the sensed pressure, and (e) means for selectively and automatically detecting the displacement of the feeler means only for a predetermined value $P_O$ of the bearing pressure of the apparatus on the material sensed by the pressure sensor, said means comprising, means for comparing the output signal of the pressure sensor with a predetermined threshold and for actuating an indicator to indicate the detected displacement of the feeler means when said output signal reaches the threshold.

2. Apparatus according to claim 1, wherein said support includes means defining a zone to bear on the material to be tested; and wherein said pressure sensor carried by the support is arranged in the zone of application of the apparatus to the material for measuring the pressure of the apparatus on said material.

3. Apparatus according to claim 2, wherein the pressure sensor provides an electrical signal whose voltage amplitude is substantially proportional to the bearing pressure of the support means on the material to be tested.

4. Apparatus according to claim 2 or 3, wherein the pressure sensor comprises a Wheatstone Bridge having two branches which are pressure-responsive elements, and wherein means are provided for energising said Wheatstone Bridge with a low frequency alternating current.

5. Apparatus according to claim 4, wherein said pressure-responsive elements are membranes carrying deposits of semi-conductor material.

6. Apparatus according to claim 1, 2 or 3, and including a displacement sensor for detecting the depth of displacement of said feeler means into the material to be tested.

7. Apparatus according to claim 6, wherein said displacement sensor comprises means for providing an output voltage of an amplitude substantially proportional to the depth displacement of the feeler means.

8. Apparatus according to claim 2 or 3, including a displacement sensor responsive to the position of said feeler means relative to said support means; and wherein (a) said feeler means is an elongate member slidable along its longitudinal axis, and (b) the pressure sensor is an annular sensor arranged symmetrically round the longitudinal axis of the feeler.

9. Apparatus according to claim 8, and including a trigger element connected to receive the output signal from said pressure sensor and to register when a voltage provided by said pressure sensor attains a predetermined value corresponding to the pressure value $P_O$, said trigger element actuating a monostable device whose output is connected to the displacement sensor such that the rising signal front at the output of the monostable device will provoke recordal of the output voltage from the displacement sensor.

10. Apparatus according to claim 9, wherein the trigger element is connected to control instants at which the output voltage from the displacement sensor is recorded.

11. Apparatus according to claim 10, including a digital voltmeter for displaying the displacement of said feeler means; and wherein the monostable device actuated by the trigger element controls, with a predetermined time delay, the display on said digital voltmeter of the voltage proportional to the displacement of said feeler means.

12. Apparatus according to claim 11, and including a bistable device connected between the trigger element an the digital voltmeter.

13. Apparatus according to claim 1, 2 or 3, wherein said indicator comprises a digital voltmeter for displaying the displacement of said feeler means.

14. Apparatus according to claims 1, 2 or 3, wherein the feeler is spring urged against the material to be tested.

* * * * *